United States Patent
Mackie et al.

(10) Patent No.: US 7,714,309 B2
(45) Date of Patent: May 11, 2010

(54) PHANTOM FOR ION RANGE DETECTION

(75) Inventors: Thomas R. Mackie, Verona, WI (US);
Ryan T. Flynn, Iowa City, IA (US);
Michael William Kissick, Madison, WI (US); Jihad H. Al-Sadah, Dhahran (SA); David C. Westerly, Madison, WI (US); Patrick M. Hill, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 237 days.

(21) Appl. No.: 12/038,697

(22) Filed: Feb. 27, 2008

(65) Prior Publication Data

US 2008/0217561 A1 Sep. 11, 2008

Related U.S. Application Data

(60) Provisional application No. 60/891,859, filed on Feb. 27, 2007.

(51) Int. Cl.
*G01N 23/225* (2006.01)
*H01J 37/147* (2006.01)
*H01J 37/30* (2006.01)

(52) U.S. Cl. .................. 250/492.3; 250/370.1; 250/309; 250/505.1; 250/390.02; 250/390.04; 382/131; 382/132; 378/21; 378/62

(58) Field of Classification Search ................. 250/306, 250/307, 309, 370.09, 370.1, 390.02, 390.03, 250/390.04, 390.12, 391, 472.1, 473.1, 492.21, 250/492.3; 378/21, 62, 65, 74, 76, 145–151, 378/901; 382/128, 131, 132

See application file for complete search history.

(56) References Cited

U.S. PATENT DOCUMENTS

| | | | |
|---|---|---|---|
| 4,276,477 A | | 6/1981 | Enge |
| 4,870,666 A | * | 9/1989 | Lonn ............................ 378/18 |
| 5,317,616 A | | 5/1994 | Swerdloff et al. |
| 5,394,452 A | | 2/1995 | Swerdloff et al. |
| 5,438,202 A | * | 8/1995 | Matanzon et al. ...... 250/363.07 |
| 5,442,675 A | | 8/1995 | Swerdloff et al. |

(Continued)

FOREIGN PATENT DOCUMENTS

DE    19907098 A1    8/2000

(Continued)

OTHER PUBLICATIONS

International Search Report, PCT Application No. PCT/US2008/055104, dated Jul. 17, 2008, ISA/EPO, 2280 HV Rijswijk, NL.

(Continued)

*Primary Examiner*—Bernard E Souw
(74) *Attorney, Agent, or Firm*—Boyle Fredrickson, S.C.

(57) ABSTRACT

A phantom for heavy ion radiation therapy provides characterization of an ion beam that may enter but not exit from the phantom. The phantom may include multiple materials and multiple spatially dispersed ion detectors to obtain signals that may be fit to known beam curves to accurately characterize the location and other parameters of Bragg peak of a given ion beam within a patient.

15 Claims, 3 Drawing Sheets

U.S. PATENT DOCUMENTS

| | | | |
|---|---|---|---|
| 5,528,650 | A | 6/1996 | Swerdloff et al. |
| 5,548,627 | A | 8/1996 | Swerdloff et al. |
| 5,625,663 | A | 4/1997 | Swerdloff et al. |
| 5,661,773 | A | 8/1997 | Swerdloff et al. |
| 5,668,371 | A * | 9/1997 | Deasy et al. ............... 850/1 |
| 5,673,300 | A | 9/1997 | Reckwerdt et al. |
| 5,724,400 | A | 3/1998 | Swerdloff et al. |
| 5,802,136 | A | 9/1998 | Carol |
| 6,345,114 | B1 * | 2/2002 | Mackie et al. ............ 382/132 |
| 6,385,286 | B1 | 5/2002 | Fitchard et al. |
| 6,438,202 | B1 | 8/2002 | Olivera et al. |
| 6,560,311 | B1 | 5/2003 | Shepard et al. |
| 6,618,467 | B1 | 9/2003 | Ruchala |
| 6,636,622 | B2 * | 10/2003 | Mackie et al. ............ 382/132 |
| 6,661,870 | B2 | 12/2003 | Kapatoes et al. |
| 6,731,970 | B2 | 5/2004 | Schlossbauer et al. |
| 6,915,005 | B1 | 7/2005 | Ruchala et al. |
| 7,046,831 | B2 | 5/2006 | Ruchala et al. |
| 7,186,986 | B2 | 3/2007 | Hinderer et al. |
| 7,207,715 | B2 | 4/2007 | Yue |
| 7,235,150 | B2 * | 6/2007 | Bischel et al. ............ 156/212 |
| 7,302,038 | B2 | 11/2007 | Mackie |
| 2002/0027970 | A1 * | 3/2002 | Chapman et al. ........... 378/62 |
| 2002/0110328 | A1 * | 8/2002 | Bischel et al. ............. 385/49 |
| 2002/0136439 | A1 | 9/2002 | Ruchala et al. |
| 2003/0160189 | A1 * | 8/2003 | Matsuda ................ 250/492.3 |
| 2003/0198319 | A1 | 10/2003 | Toth et al. |
| 2004/0105611 | A1 * | 6/2004 | Bischel et al. ............. 385/14 |
| 2005/0046928 | A1 * | 3/2005 | Bischel et al. ........... 359/341.3 |
| 2005/0123092 | A1 | 6/2005 | Mistretta et al. |
| 2005/0197564 | A1 | 9/2005 | Dempsey |
| 2006/0226372 | A1 * | 10/2006 | Yanagisawa et al. .... 250/396 R |
| 2006/0285639 | A1 | 12/2006 | Olivera et al. |
| 2007/0029510 | A1 | 2/2007 | Hermann |
| 2007/0036267 | A1 | 2/2007 | Becker et al. |
| 2007/0041494 | A1 | 2/2007 | Ruchala et al. |
| 2007/0041495 | A1 | 2/2007 | Olivera et al. |
| 2007/0041496 | A1 | 2/2007 | Olivera et al. |
| 2007/0041497 | A1 | 2/2007 | Schnarr et al. |
| 2007/0041498 | A1 | 2/2007 | Olivera et al. |
| 2007/0041499 | A1 | 2/2007 | Lu et al. |
| 2007/0041500 | A1 | 2/2007 | Olivera et al. |
| 2007/0043286 | A1 * | 2/2007 | Lu et al. .................. 600/407 |
| 2007/0076846 | A1 | 4/2007 | Ruchala et al. |
| 2007/0104316 | A1 | 5/2007 | Ruchala et al. |
| 2007/0195922 | A1 | 8/2007 | Mackie et al. |
| 2007/0195929 | A1 | 8/2007 | Ruchala et al. |
| 2007/0195930 | A1 | 8/2007 | Kapatoes et al. |
| 2007/0242801 | A1 | 10/2007 | Mackie et al. |
| 2007/0248139 | A1 * | 10/2007 | Bischel et al. .............. 372/75 |
| 2008/0217561 | A1 * | 9/2008 | Mackie et al. ........... 250/492.3 |
| 2009/0274273 | A1 * | 11/2009 | Von Neubeck et al. ........ 378/65 |

FOREIGN PATENT DOCUMENTS

| | | | |
|---|---|---|---|
| EP | 0986070 | A | 3/2000 |
| EP | 1045399 | A | 10/2000 |
| JP | 2000 214298 | A | 8/2000 |
| WO | WO02/07817 | A | 1/2002 |
| WO | WO02/41948 | A | 5/2002 |
| WO | WO2005/004168 | A | 1/2005 |
| WO | WO2007/021226 | A | 2/2007 |

OTHER PUBLICATIONS

International Search Report, PCT Application No. PCT/US2008/055070, dated Jul. 17, 2008, ISA/EPO, 2280 HV Rijswijk, NL.

International Search Report, PCT Application No. PCT/US2008/055069, dated Jul. 17, 2008, ISA/EPO, 2280 HV Rijswijk, NL.

International Search Report, PCT Application No. PCT/US2008/055161, dated Jul. 17, 2008, ISA/EPO, 2280 HV Rijswijk, NL.

International Search Report, PCT Application No. PCT/US2008/055083, dated Jul. 17, 2008, ISA/EPO, 2280 HV Rijswijk, NL.

International Search Report, PCT Application No. PCT/US2008/055096 dated Jul. 17, 2008, ISA/EPO, 2280 HV Rijswijk, NL.

International Search Report, PCT Application No. PCT/US2008/055090 dated Jul. 17, 2008, ISA/EPO, 2280 HV Rijswijk, NL.

International Search Report, PCT Application No. PCT/US2008/055147, dated Jul. 25, 2008, ISA/EPO, 2280 HV Rijswijk, NL.

Baumert, BG, et al., Dose conformation of intensity-modulated stereotactic photon beams, proton beams, and intensity-modulated proton beams for intracranial lesions, Int. J. Radiat. Oncol. Biol. Phys., 2005, 60:1314-1324, Elsevier, Amsterdam, Netherlands.

Deasy, JO, et al., Distal edge tracking: a proposed delivery method for conformal proton therapy using intensity modulation, 1997, pp. 406-409, Proceedings of the XIIth International Congress on Computers in Radiotherapy May 27-30, 1997, Salt Lake City, IEEE Publishing, Los Alamitos, California, USA.

Deasy, JO, A proton dose calculation algorithm for conformal therapy simulations based on Moliere theory of lateral deflections, Med. Phys., Apr. 1998, 25:476-483, American Association of Physical Medicine, New York, New York.

Lomax, AJ, Intensity modulation methods for proton radiotherapy, Phys. Med. Biol., 1999 44:185-205, IOP Publishing Ltd., Bristol, UK.

Lomax, AJ, et al. Intensity modulated proton therapy: A clinical example, Mar. 2001, Med. Phys. 28:317-324, , American Association of Physical Medicine, New York, New York.

Lomax, AJ, Compensated and intensity-modulated proton therapy, in Palta J, and Mackie TR (eds), Intensity Modulated Radiation Therapy: The State of the Art, Nov. 2004, pp. 787-828, Medical Physics Publishing Madison, WI.

Lomax, AJ, et al., Treatment planning and verification of proton therapy using spot scanning: initial experiences. 2004a, Med. Phys. 31:3150-3157, American Association of Physical Medicine, New York, New York.

Lomax, AJ, et al., The clinical potential of intensity modulated proton therapy, 2004b, Z. Med. Phys. 14:147-152, Elsevier, Amsterdam, Netherlands.

Kanai, T, et al., Spot scanning system for proton radiotherapy, Jul./Aug. 1980, Med. Phys 7:365-369, American Association of Physical Medicine, New York, New York.

Moyers MF, (Proton therapy, Van Dyk (ed), The Modern Technology of Radiation Oncology, 1999, pp. 823-869, Medical Physics Publishing, Madison, WI.

Nill, S, et al., Inverse planning of intensity modulated proton therapy, 2004, Z Med. Phys. 14:35-40, Elsevier, Amsterdam, Netherlands.

Oelfke U, et al., Intensity modulated radiotherapy with charged particle beams: Studies of inverse treatment planning for rotation therapy. Jun. 2000, Med. Phys, 27:1246-1257, American Association of Physical Medicine, New York, New York.

Paganetti H, Proton Therapy: A Workshop Handout. 2005, Private Communication, Massachusetts General Hospital, Boston, MA.

Sampayan S, et al. Development of a compact radiography accelerator using dielectric wall accelerator technology, Jun. 6, 2005, Proceed. Int. Pulsed Power Conf. Monterey, CA, Lawrence Livermore Laboratory, Livermore, CA.

Wilson RW., Radiological use of fast protons. Nov. 1946, Radiology 47:487-491, Radiological Society of North America, Easton, Pennsylvania.

Yu C., Intensity modulated arc therapy with dynamic multileaf collimation: an alternative to tomotherapy, 1995, Phys. Med. Biol. 40:1435-1449, IOP Publishing Ltd., Bristol, UK.

Anderov V., Combined X-Y scanning magnet for conformal proton radiation therapy, Med. Phys. , Mar. 2005, 32:815-818, American Association of Physical Medicine, New York, New York.

Goitlein, M., Beam scanning for heavy charged particle radiotherapy, Nov./Dec. 1983, Med. Phys. 10 (6) pp. 831-840, American Association of Physical Medicine, New York, New York.

* cited by examiner

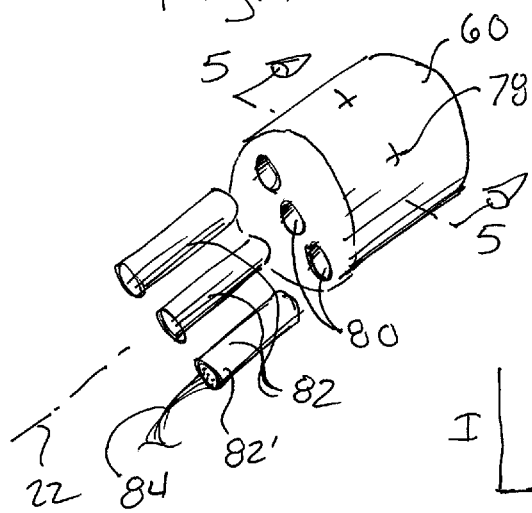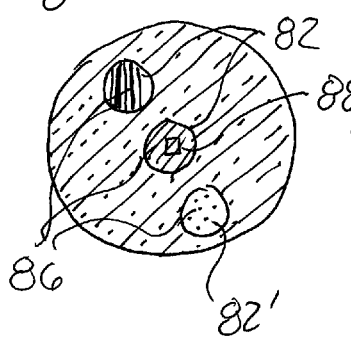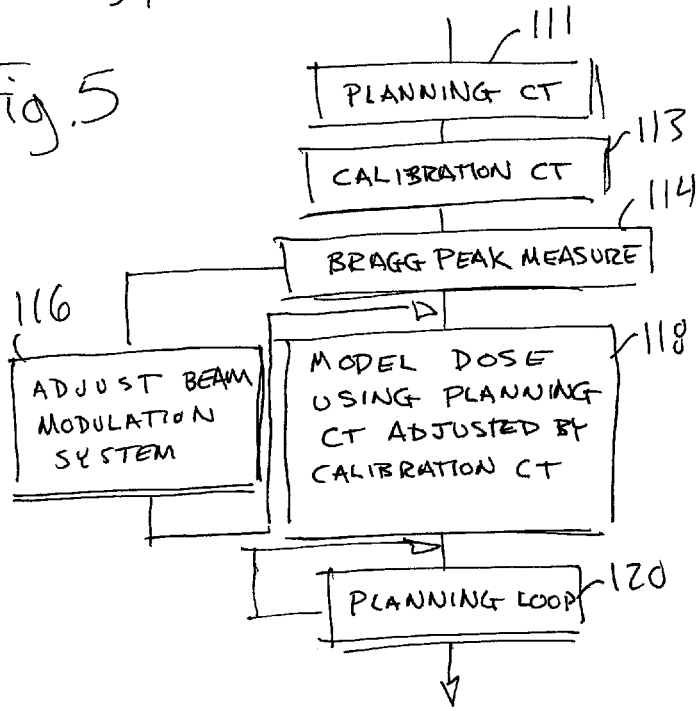

PHANTOM FOR ION RANGE DETECTION

CROSS REFERENCE TO RELATED APPLICATION

This application claims the benefit of U.S. Provisional Application 60/891,859, filed Feb. 27, 2007, the disclosure of which is incorporated herein by reference.

This invention was made with United States government support awarded by the following agency:

NIH CA088960

The United States government has certain fights in this invention.

BACKGROUND OF THE INVENTION

The present invention relates to radiotherapy systems using ions for the treatment of cancer and the like and, in particular, to a phantom for such systems.

External beam radiation therapy may treat a tumor within the patient by directing high-energy radiation in one or more beams toward the tumor. Recent advance external beam radiation systems, for example, as manufactured by Tomotherapy, Inc., treat the tumor with multiple x-ray fan beams directed at the patient over an angular range of 360°. Each of the beams is comprised of individually modulated rays whose intensities can be controlled so that the combined affect of the rays over the range of angles provides an arbitrarily complex treatment area with minimized skin dose.

The benefit of the improved accuracy possible with such systems is ensured by careful characterization and monitoring of the x-ray beam geometry and intensity, for example, through portal imaging devices and entrance dose monitors.

X-rays expose tissue not only within the tumor but also along the path of each ray into and out of the patient. While judicious selection of the angles and intensities of the rays of x-ray radiation can limit radiation dose outside of the tumor, a desire to more closely conform the radiation dose to the tumor has raised interest in substituting ions such as protons for x-ray radiation. Unlike x-rays, the dose deposited by a proton beam is not uniform in homogenous tissue, but rises substantially, at the "Bragg peak" just before the proton stops within the tissue. Further, because the proton can be controlled to stop within the tissue, exit does from the proton beam can be substantially eliminated. These two features allow improved placement of dose within the tumor.

Unfortunately, unlike x-rays, ions are not easily characterized by entrance dose monitors and portal imaging device. In part, this is because such devices are sensitive largely to flux (photons per unit time) as opposed to radiation energy, and it is this latter characteristic which determines the important quality of proton range. Portal imaging systems, which rely on radiation exiting the patient, are of limited value in a proton imaging system in which the protons stop within the patient.

SUMMARY OF THE INVENTION

The present invention provides a phantom that may characterize the energy and hence the range of protons. The phantom uses a one or more tissue-mimicking material and an array of intensity detecting elements whose pattern of intensities may locate the Bragg peak. The location of the Bragg peak, in turn, reveals the proton energies. The phantom may be used to calibrate a proton or heavy ion therapy machine and/or may be used to better characterize a CT image used for treatment planning, by equating CT numbers to materials that have been characterized with respect to their interaction with protons.

Specifically then, the present invention provides a phantom including a tissue-mimicking support and a set of ion detectors spatially separated within the tissue-mimicking support to detect passage of ions through the tissue-mimicking support. A data processing system receiving signals from the ion detectors deduces a location within the phantom of a Bragg peak of ions passing through the tissue-mimicking support.

Thus it is one aspect of the invention to provide a measurement system suitable for next-generation ion radiation therapy machines to provide accurate characterization of the ion beam energies.

The tissue-mimicking support may include removable portions wherein the ion detectors are held within one removable portion to be repositioned within the tissue-mimicking support. The removable portions may provide materials representing different tissue types so that portions may mimic different tissue types.

It is thus an aspect of at least one embodiment of the invention to provide a phantom that can characterize the effect of different materials and material thicknesses on Bragg peak location. It is another aspect of at least one embodiment of the invention to allow the phantom to be configured to approximate the actual treatment volume.

The tissue-mimicking support may include fiducial markers allowing automated identification of the different materials in a CT image.

It is thus another object of the invention to allow the phantom to be used to calibrate planning CT images.

The ion detectors may be arrayed both along a direction of propagation of the ion beam and across the direction of propagation of the ion beam and the data processing system may fit a template multidimensional Bragg peak to the signals and spatial locations of the ion detectors to identify the Bragg peak.

It is thus an aspect of the present invention to provide for multidimensional characterization of the Bragg peak including range and beam widening. It is another aspect of the invention to allow characterization of the beam center line.

These particular features and advantages may apply to only some embodiments falling within the claims and thus do not define the scope of the invention.

BRIEF DESCRIPTION OF THE DRAWINGS

FIG. 4 is a perspective view of a phantom positionable in place of the patient of FIG. 2, the phantom having removable plugs of tissue-mimicking material held by a larger tissue-mimicking support, and further showing one plug as instrumented with ion detectors;

FIG. 5 is a cross-section along line 5-5 of FIG. 4 showing a configuration of the plugs inserted into the phantom and showing a radio opaque fiducial marker on one plug for CT identification;

FIG. 6 is an elevational, cross section of the plug instrumented with ion detectors showing a centerline of an ion beam through detector elements, and a plot of the signals from the elements as fit to a Bragg peak of the ion beam;

FIG. 9 is a flow chart for use of the phantom of the present invention for calibrating the gantry system and/or for treatment planning.

DETAILED DESCRIPTION OF THE PREFERRED EMBODIMENT

Figure 1:
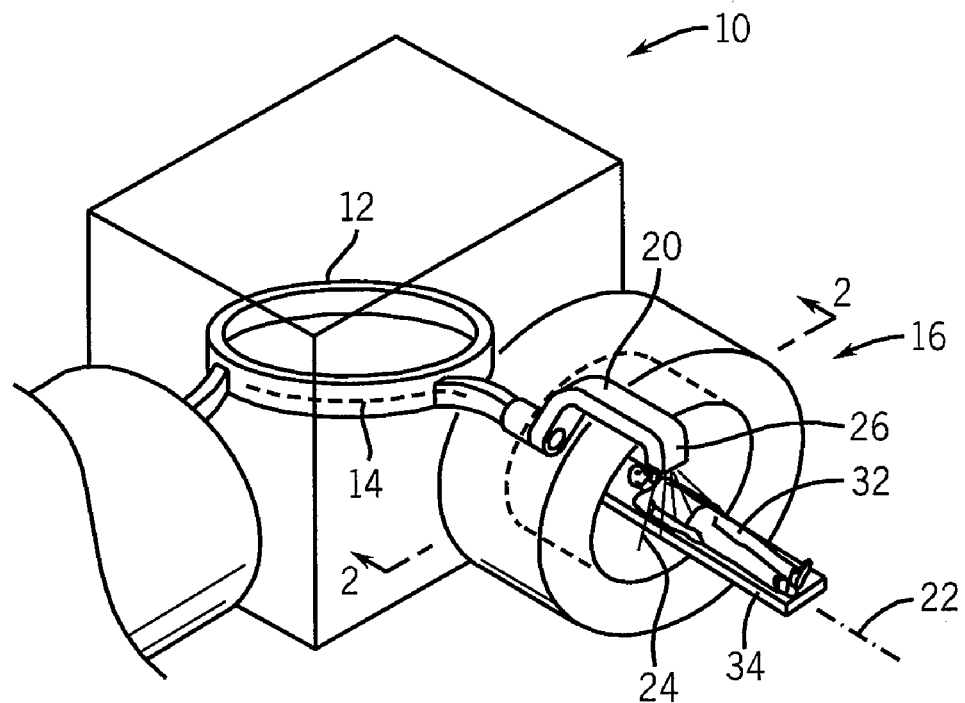
FIG. 1 is a perspective view in partial phantom of an example proton therapy system suitable for use with the present invention having a synchrotron proton source providing protons to multiple gantry units.

Referring now to FIG. 1, a ion therapy system 10 may include a cyclotron or synchrotron 12 or other proton source providing a pencil beam of protons 14 to a gantry unit 16.

Figure 2:
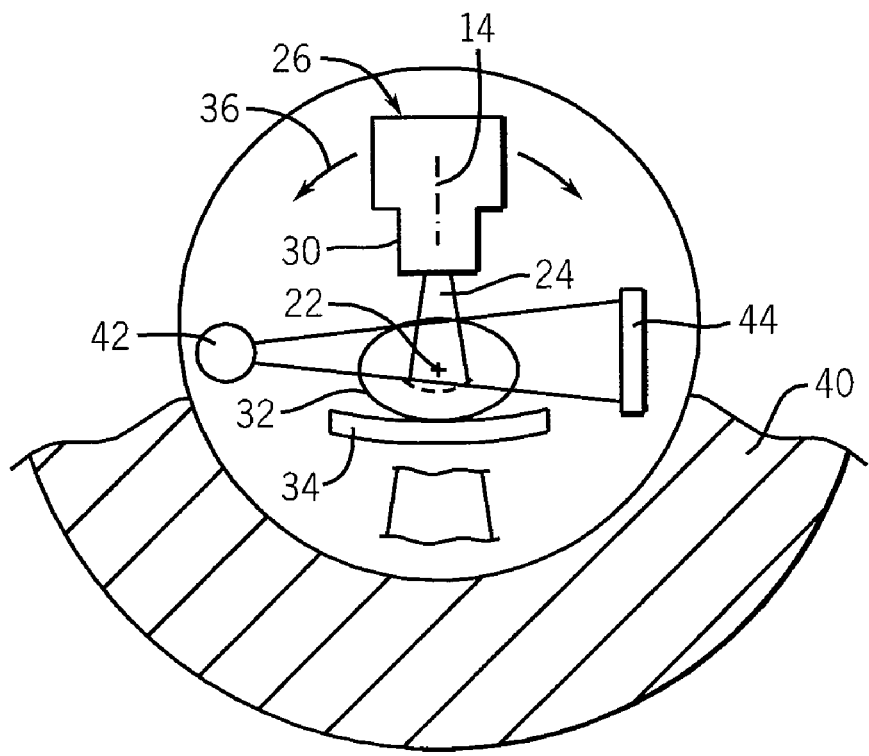
FIG. 2 is a cross-section along line 2-2 of FIG. 1 showing a proton beam modified by a beam control system before being directed into a patient.

Referring also to FIG. 2, the proton beam 14 may be received along an axis 22 into an axial portion of a rotating arm 20 rotating about the axis 22. The rotating arm 20 includes guiding magnet assemblies of a type known in the art to bend the proton beam 14 radially away from the axis 22 then parallel but spaced from the axis 22 to a treatment head 26. The treatment head 26 orbits about the axis 22c with rotation of the rotating arm 20 bending the proton beam 14 back toward the axis 22.

The treatment head 26 may include a modulation assembly 30 for forming the proton beam 14 into a wider treatment beam (for example a fan or cone beam) and for modulating rays of the beam in energy and intensity to produce a modulated treatment beam 24 as will be described.

Referring still to FIG. 2, a patient 32 may be positioned on a support table 34 extending along the axis 22 so that a modulated treatment beam 24 may irradiate the patient 32 at a variety of angles 36 about the axis 22. A cylindrical neutron shield 40 having a bore for receiving the table 34 and the rotating arm 20 may surround the gantry unit 16 to block generated neutrons.

In one embodiment, a second rotating arm (not shown) may rotate with or independently of the rotating arm 20 to support an x-ray source 42 and x-ray detector 44 opposed across the axis 22 to illuminate the patient 32 at a range of angles to provide a CT scan of the patient 32 according to techniques well-known in the art.

Figure 3:
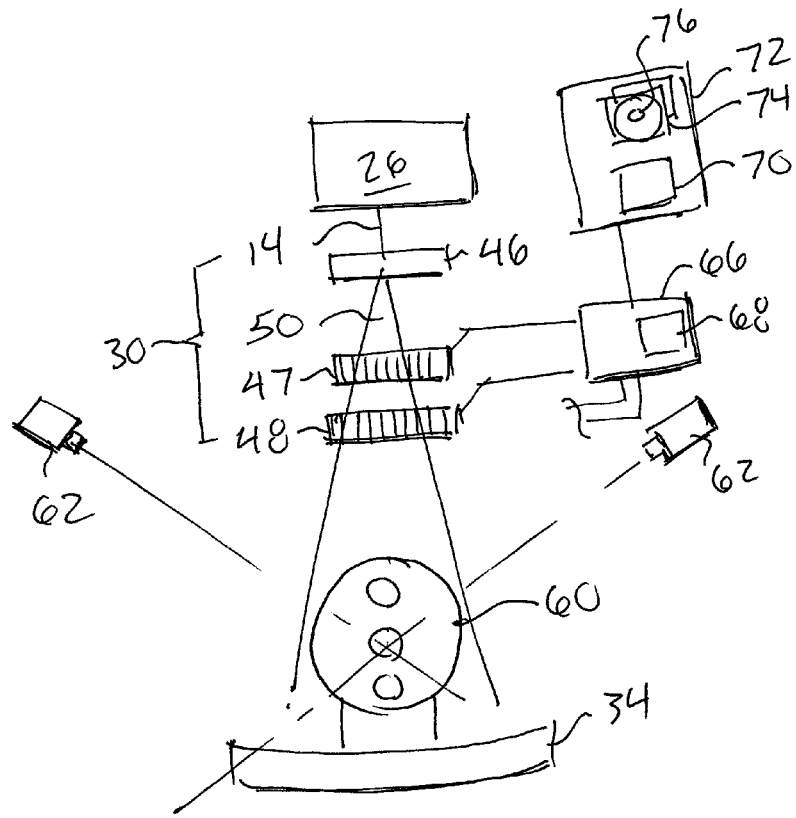
FIG. 3 is a block diagram of the beam control system of FIG. 2.

Referring now to FIG. 3, the modulation assembly 30 may include a fan beam former 46, followed by an energy or range modulator 47, followed in turn by an intensity modulator 48. The fan beam former 46 may receive the monoenergetic pencil beam of protons 14 having a generally small circular cross-section to widen this beam into a treatment beam 50 being for example a larger circle (a cone beam) or a thin rectangle extending perpendicular to axis 22 (a fan beam). The range modulator 47, receives the treatment beam 50 and changes the energy of the protons in different rays 52 of the treatment beam 50, for example by selective insertion of different thicknesses of materials as taught in U.S. Pat. No. 5,668,371 entitled: "Method and Apparatus for Proton Therapy" assigned to the same assignee as the present invention, and hereby incorporated by reference.

The treatment beam 50 then is received by the intensity modulator 48 which may, for example, be a set of shutters, one for each ray 52, controlling the amount of time the protons may pass along that ray 52 thus defining an average intensity of protons in each ray 52 as it also taught by the above referenced patent.

The modulated treatment beam 24 having rays 52 that are both intensity and energy modulated may be directed toward a phantom 60 of the present invention fixed at a known location with respect to the table 34. This precise location of the phantom may be assisted by means of laser line projectors 62 directing lasers toward an isocenter along axis 22, the isocenter being 64 defining the center of rotation of the treatment head 26 and matching with fiducial markings on the outside of the phantom 60 as will be described.

The range modulator 47 and intensity modulator 48 may be controlled by a control system 66 including a calibration memory 68 providing a conversion between the desired intensity and actual physical shutter settings of the range modulator 47 and intensity modulator 48. The control system 66 may receive a treatment plan 70 from a general purpose computer 72 executing a stored program as will the described to generate the treatment plan from one or more CT images 74 having a user-defined dose pattern 76 superimposed thereon. Computer 72 may also provide for a CT reconstruction by controlling and monitoring of x-ray source 42 and detector 44 described above and may provide other control functions generally understood in the arc.

Referring now to FIG. 4 the phantom 60 may for example be generally cylindrical with the axis of the cylinder aligned, when it is placed on the table 34, with axis 22. And outer surface of the cylinder may include fiducial markings 78 that may align with the laser scans of laser line projectors 62 to allow precise and known placement of the phantom on the table 34 and thus its location with respect to the treatment head 26. The phantom in one embodiment may include a set of axial bores 80 of cylindrical dimension that may receive corresponding cylindrical inserts 82. The main body of the phantom 60 may be, for example, a water mimicking material such as Plexiglas or polyethylene or other hydrocarbon material while the inserts may be of the same material or different materials for example those simulating bone or lungs, these latter materials compounding, for example, calcium and phosphorus compounds mixed in with plastic or micro spheres to provide for air inclusions decreasing the density of the plastic material.

One of the inserts 82 may be a detection insert 82' providing a series of ion detectors or MOSFET or scintillation detectors embedded in the insert 82' and communicating through cabling 84 with a data acquisition system associated with computer 72, as shown in FIG. 3, or a freestanding data acquisition system.

Referring now to FIG. 5, a CT image of the phantom 60 will provide for image areas 86 associated with the main body of the phantom 60 and each of the inserts 82. Each image area may provide a characteristic CT number or image grayscale value. The inserts 82 may include radio-opaque fiducial markings 88, for example, allowing them to be automatically recognized in the CT image, for example, as may be fashioned from as lead beads or wire. Improved discernment of the type of material may be provided, for example, through dual energy CT techniques or the like.

Referring now to FIG. 6, a ray 52 extending along a ray axis 90 may pass through the plug 82' to be measured by one or more detector elements 92. Each of these detector elements 92 provides a signal 94 having a strength I and a spatial location x. The spatial location will generally describe up to three dimensions, but as shown is a single dimension along the known axis 90. These signals 94 may be fit to a Bragg peak template 96 having a characteristic shape that may be scaled in the x and I dimensions to provide a best fit to the signals 94. Once the Bragg peak template is fit to the signals 94, Bragg peak maximum 98 and Bragg peak location 100 may then be determined.

Figure 7:
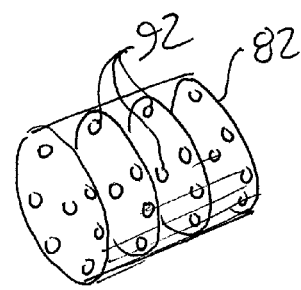
FIG. 7 is a perspective view of a three-dimensional array of detector elements.

Referring now to FIG. 7 the detector elements 92 may be distributed in three dimensions within the plug 82' to provide not only a Bragg peak location but a three-dimensional characterization of the proton beam distribution.

Figure 8:
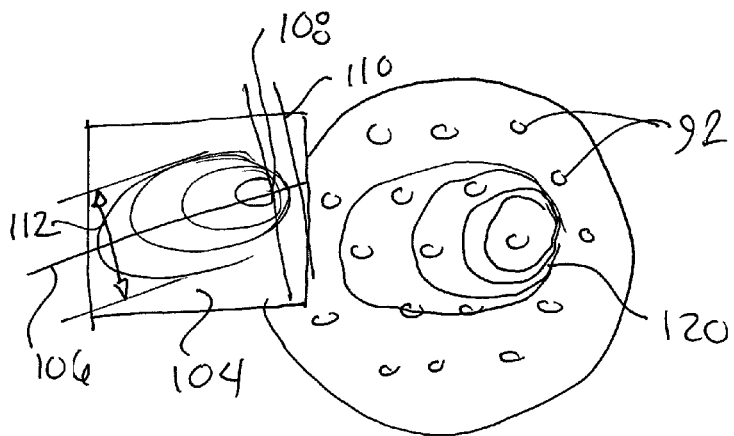
FIG. 8 is a plot of isodose lines for a standard Bragg peak being part of a set of isodose surfaces that may be fit to the isodose surfaces measured by the detector of FIG. 7 to locate the Bragg peak in the phantom.

Referring now to FIG. 8 a two-dimensional implementation of this process for example takes the signals 94 from each of the detectors in multiple dimensions to generate an isodose surface 102 which may be fit to a template standard isodose surface 104 with scaling, translation and rotation which may be used to determine proton beam characteristics including beam axis 106, beam peak 108, beam limit 110, and beam width 112 byte reading from the template as so scaled, translated, and rotated. It will be understood that this process may be readily extended to a complete three-dimensional characterization of the proton beam even though the beam does not exit the phantom 60.

Referring now to FIG. 9, the phantom 60 may be used in a procedure with the system of FIG. 1 to provide improved characterization of the ion beam and of the patient for planning purposes. At a first process block 111, a planning CT images taken of the patient in a manner similar to that done for standard x-ray Tomotherapy. This is followed or preceded by a calibration CT scan indicated by process block 113 of the phantom 60.

As indicated by process block 114, the radiation therapy machine 10 is then used to irradiate the phantom 60 to determine the Bragg peak location for the phantom 60 as calibrated at step 113. This Bragg peak information is used for two purposes. In its initial purpose, as indicated by process block 116, the Bragg peak measurements are extracted and used as to adjust and calibrate the modulation assembly 30 through, for example, adjustment of calibration factor table 68 described with respect to FIG. 3. In this way the radiation therapy machine can produces the energies and beam spread expected in its operation.

The Bragg peak information is also used as indicated by process block 118 to improve the radiation planning process. In this use, materials of the planning CT of the patient taken at process block 111 are matched to the known materials on the phantom 60 by matching grayscale values of the calibration CT image taken at process block 113 with the planning CT image taken at process block 111. An improved model of the patient is thereby produced and used to evaluate different beam intensities and ranges according to a planning loop 120 which in its simplest form uses a Monte Carlo or simple similar technique to perturb intensities and ranges of the beams and to model those iteratively against the model produced. Alternatively as disclosed in the previously cited U.S. Pat. No. 5,668,371 the beam ranges may be placed using distal edge algorithm described in that patent and the intensities alone may be iteratively modeled using the attenuating properties all the materials alone.

It is specifically intended that the present invention not be limited to the embodiments and illustrations contained herein, but include modified forms of those embodiments including portions of the embodiments and combinations of elements of different embodiments as come within the scope of the following claims.

We claim:

1. A ion phantom comprising:
  a tissue-mimicking support;
  a set of ion detectors spatially separated with in the tissue-mimicking support to detect passage of ions through the tissue-mimicking support; and
  a data processing system receiving signals from the ion detectors to deduce a location within the phantom of a Bragg peak of ions passing through the tissue-mimicking support.

2. The ion phantom of claim 1 wherein the tissue-mimicking support includes removable portions and wherein the ion detectors are held within one removable portion to be repositioned within the tissue-mimicking support.

3. The ion phantom of claim 2 wherein the removable portions provide materials representing different tissue types so that portions may mimic different tissue types.

4. The ion phantom of claim 1 wherein the tissue-mimicking support includes different materials mimicking of different tissue types.

5. The ion phantom of claim 4 wherein the tissue-mimicking support further includes fiducial markers allowing automated identification of the different materials in a CT image.

6. The ion phantom of claim 1 wherein the ion detectors are arrayed both along a direction of propagation of the ion beam and across the direction of propagation of the ion beam and wherein the data processing system fits a standard multidimensional Bragg peak to the signals and spatial locations of the ion detectors to identify the Bragg peak.

7. The ion phantom of claim 1 wherein the ion detectors are arrayed both along a direction of propagation of the ion beam and across the direction of propagation of the ion beam and wherein the data processing system receives the signals from the ion detectors to deduce a centerline of the ion beam.

8. A ion therapy apparatus comprising:
  a ion beam source;
  a modulation system receiving control signal and ions from the beam source to provide a set of spatially separated ion beams modulated in energy and intensity according to the control signal;

a phantom positionable within the ion beams and providing a set of ion detectors within a tissue-mimicking support;

a data processing system receiving signals from the ion detectors to deduce a Bragg peak of at least one ion beam within the phantom; and a control signal adjuster receiving Bragg peak data from the data processing system to adjust the modulation system.

9. The ion therapy apparatus of claim 8 wherein the tissue-mimicking support includes removable portions and wherein the ion detectors are held within one removable portion to be repositioned within the tissue-mimicking support.

10. The ion therapy apparatus of claim 9 wherein the removable portions provide materials representing different tissue types so that portions may mimic different tissue types.

11. The ion therapy apparatus of claim 8 wherein the tissue-mimicking support includes different materials mimicking of different tissue types.

12. The ion therapy apparatus of claim 8 wherein the ion detectors are arrayed both along a direction of propagation of the ion beam and across the direction of propagation of the ion beam and wherein the data processing system fits a standard multidimensional Bragg peak to the signals and spatial locations of the ion detectors to identify the Bragg peak.

13. The ion therapy apparatus of claim 8 wherein the ion detectors are arrayed both along a direction of propagation of the ion beam and across the direction of propagation of the ion beam and wherein the data processing system receives the signals from the ion detectors to deduce a centerline of the ion beam.

14. A ion therapy system comprising:

a phantom providing a series of different tissue-mimicking materials;

a computed tomography system for obtaining a CT image of a treatment volume of a patient and of the phantom;

a dose identification tool receiving input from a user to demarcate a desired dose to the treatment volume with respect to the CT image;

a treatment plan calculator receiving the desired dose and the CT image of the phantom end of the patient, the treatment plan calculator operating to:

(i) model tissue characteristics of the treatment volume with respects to an ion beam using materials of the phantom matching within the CT images of the patient and the phantom; and (ii) determine a treatment plan using the model;

a modulatable ion beam source for irradiating the treatment volume with ions according to the treatment plan.

15. The ion phantom of claim 14 wherein the phantom further includes fiducial markers allowing automated identification of the different tissue-mimicking materials in the CT image of the phantom.

* * * * *